(12) United States Patent
Otsuki et al.

(10) Patent No.: US 8,528,424 B2
(45) Date of Patent: Sep. 10, 2013

(54) EXHAUST GAS ANALYZING SYSTEM

(75) Inventors: Yoshinori Otsuki, Kyoto (JP);
Masayoshi Shinohara, Kyoto (JP);
Kazuo Hanada, Kyoto (JP)

(73) Assignee: Horiba, Ltd., Kyoto (JP)

( * ) Notice: Subject to any disclaimer, the term of this patent is extended or adjusted under 35 U.S.C. 154(b) by 150 days.

(21) Appl. No.: 13/189,069

(22) Filed: Jul. 22, 2011

(65) Prior Publication Data

US 2012/0017666 A1 Jan. 26, 2012

(30) Foreign Application Priority Data

Jul. 23, 2010 (JP) ................................ 2010-166435

(51) Int. Cl.
*G01N 1/00* (2006.01)
(52) U.S. Cl.
USPC .................. 73/863.03; 73/863.51; 73/863.71
(58) Field of Classification Search
USPC ............... 73/863.03, 863.51, 863.53, 863.58, 73/863.71, 863.91
See application file for complete search history.

(56) References Cited

U.S. PATENT DOCUMENTS

| | | | | |
|---|---|---|---|---|
| 3,406,562 | A * | 10/1968 | Perna, Jr. et al. | 73/23.31 |
| 4,633,706 | A * | 1/1987 | Ito et al. | 73/23.33 |
| 4,747,297 | A * | 5/1988 | Okayama et al. | 73/23.33 |
| 4,814,143 | A * | 3/1989 | Kojima et al. | 422/83 |
| 4,916,384 | A * | 4/1990 | Ishida | 324/71.4 |
| 5,052,425 | A * | 10/1991 | Hohenberg et al. | 137/1 |
| 5,187,972 | A | 2/1993 | DeFriez | |
| 5,410,907 | A * | 5/1995 | Strom et al. | 73/23.31 |
| 5,469,731 | A * | 11/1995 | Decker et al. | 73/23.31 |
| 5,486,220 | A * | 1/1996 | Honda et al. | 55/487 |
| 5,621,166 | A * | 4/1997 | Butler | 73/114.71 |
| 6,058,789 | A * | 5/2000 | Kohsaka et al. | 73/863.11 |
| 6,134,942 | A * | 10/2000 | Pasquereau et al. | 73/23.31 |
| 6,178,830 | B1 * | 1/2001 | Freud | 73/863.51 |
| 6,481,299 | B2 * | 11/2002 | Silvis et al. | 73/863.81 |
| 6,725,653 | B2 * | 4/2004 | Brown et al. | 60/297 |
| 6,823,268 | B2 * | 11/2004 | Silvis et al. | 702/30 |
| 6,823,748 | B2 * | 11/2004 | Silvis et al. | 73/863.03 |
| 7,191,671 | B2 * | 3/2007 | Kreft | 73/863.81 |
| 7,434,449 | B2 * | 10/2008 | Kusaka et al. | 73/23.31 |

(Continued)

FOREIGN PATENT DOCUMENTS

| | | |
|---|---|---|
| EP | 0656539 A1 | 6/1995 |
| EP | 1207390 A2 | 5/2002 |

(Continued)

*Primary Examiner* — David A Rogers
(74) *Attorney, Agent, or Firm* — Brooks Kushman P.C.

(57) ABSTRACT

In a gas analyzer 3 and a gas analyzing system 100 adapted to introduce and analyze a part of a measurement target gas flowing through a measurement target gas flow passage 12, in order to ensure accuracy in controlling the measurement target gas flowing through the measurement target gas flow passage 12 and accuracy in its own and other measurements, there are provided an object measurement device 35 adapted to acquire a part of the measurement target gas introduced from the measurement target gas flow passage 12 so as to measure a quantity etc. of a measurement object contained in the measurement target gas, an acquired gas flow rate measurement device 34 adapted to measure a flow rate of the measurement target gas acquired by the object measurement device 35, and a gas supply device 36 adapted to supply another gas of a flow rate equal to the gas flow rate measured by the acquired gas flow rate measurement device 34 to a portion downstream of a shunt point in the measurement target gas flow passage 12.

6 Claims, 3 Drawing Sheets

(56) References Cited

U.S. PATENT DOCUMENTS

| | | | |
|---|---|---|---|
| 7,610,793 B2* | 11/2009 | Liu et al. | 73/28.01 |
| 7,665,375 B2* | 2/2010 | Wei et al. | 73/865.5 |
| 2002/0020232 A1* | 2/2002 | Yamagishi et al. | 73/863.11 |
| 2005/0109128 A1* | 5/2005 | Pasquereau et al. | 73/863.21 |
| 2005/0160838 A1* | 7/2005 | Weaver | 73/863.03 |
| 2011/0048105 A1* | 3/2011 | Graze, Jr. | 73/23.31 |

FOREIGN PATENT DOCUMENTS

| | | | |
|---|---|---|---|
| JP | 64031032 A | * | 2/1989 |
| JP | 03-218436 | | 9/1991 |
| JP | 08254487 A | * | 10/1996 |
| JP | 08278237 A | * | 10/1996 |
| JP | 2000028499 A | * | 1/2000 |
| JP | 2000292322 A | * | 10/2000 |
| JP | 2000329661 A | * | 11/2000 |

* cited by examiner

EXHAUST GAS ANALYZING SYSTEM

CROSS-REFERENCE TO RELATED APPLICATION

This application claims priority to Japanese Patent Application No. 2010-166435 filed Jul. 23, 2010, the disclosure of which is incorporated in its entirety by reference herein.

TECHNICAL FIELD

The present invention relates to a gas analyzer and a gas analyzing system for measuring particulate matter contained in an exhaust gas discharged from an engine.

BACKGROUND ART

In order to analyze a gas to be measured (referred to as "measurement target gas" hereinafter) flowing through a measurement target gas flow passage, if a part thereof is shunted to be measured, a flow rate in the measurement target gas flow passage is reduced in correspondence with a shunted flow rate, and this affects a control of the measurement target gas and its own and other measurements and may likely lead to a trouble in some cases.

For example, in Patent Literature 1, disclosed is a configuration that an exhaust gas discharged from an internal combustion engine is diluted with a dilution gas and the diluted exhaust gas (i.e., measurement target gas) is led to flow into a mini-tunnel (i.e., measurement target gas flow passage) and a part of the diluted exhaust gas is shunted to be led to a smoke particle measurement device. In this smoke particle measurement device, the smoke particles (also, referred to as "particulate matter" hereinafter) contained in the diluted exhaust gas are collected by a collecting filter so as to measure a mass thereof.

In this configuration, by locating a CVS device downstream of the mini-tunnel, the flow rate of the diluted exhaust gas flowing in the mini-tunnel is controlled to be constant and an introduction flow rate of the exhaust gas into the mini-tunnel can be controlled. This is because, by controlling the introduction flow rate of the dilution gas into the mini-tunnel, the introduction flow rate of the exhaust gas into the mini-tunnel is indirectly controlled.

By the way, the flow rate control mentioned above is implemented on the premise that the flow rate of the gas to be introduced into the mini-tunnel, i.e., measurement target gas flow passage is equal to a flow rate of the gas derived therefrom. Therefore, if the smoke particle measurement device takes in a part of the diluted exhaust gas from the mini-tunnel by shunting, there occurs an error in the introduction flow rate of the exhaust gas into the mini-tunnel accordingly, and this may also lead to occurrence of an error in a control of a dilution ratio of the exhaust gas and a measurement in the CVS device and the like.

Therefore, in Patent Literature 1, the diluted exhaust gas derived from the smoke particle measurement device after the smoke particles are collected is entirely led to reflow to the mini-tunnel so as to eliminate the error. In Patent Literature 1, as described in the second paragraph of column 2 at page 4 and FIG. 1 therein, prior to lead the diluted exhaust gas from the smoke particle measurement device to reflow, an appropriate flow rate of air is previously rendered flowing in a reflow passage, and when the diluted exhaust gas is rendered to flow back, a valve is switched to shut off the air. It seems that a large pressure fluctuation may not occur in the mini-tunnel at the time of starting the reflow.

However, as disclosed in Patent Literature 1, if it is configured that the measurement target gas subjected to a measurement can be returned as it is to the flow passage of the measurement target gas, the measurement errors etc. can be avoided by forming the reflow, but there may be nevertheless a case where the measurement target gas cannot be returned to the flow passage of the measurement target gas in such a case where the measurement target gas is diluted or absorbed according to a measurement device.

For example, in a particulate matter counting device for counting the number of the particulate matter, since the acquired measurement target gas is diluted within the device, the measurement target gas cannot be returned as it is. Conventionally, since the flow rate of the measurement target gas to be acquired by such a particulate matter counting device is not so large in amount compared to a flow rate of the measurement target gas flowing through the flow passage of the measurement target gas, if a small in amount, the error can be suppressed within a tolerance range even if the measurement target gas is not returned. However, in recent years, it is required to further improve a measurement accuracy and in the case where the flow rate of the measurement target gas flowing through the flow passage of the measurement target gas such as a micro-tunnel, it becomes impossible to suppress an error of such as a dilution ratio in an admissible range due to the fact that the measurement target gas cannot be returned to the source flow passage.

To give a specific numerical example, conventionally, the flow rate of the measurement target gas (diluted exhaust gas) acquired by, e.g., the particulate matter counting device is in a range of 0.1 to 0.5 L/min and the flow rate of the diluted exhaust gas flowing in the CVS device is set to 50 L/min. Then, there may occur an error in a dilution ratio of the diluted exhaust gas in a degree of 1% (=0.5/50) at the maximum. In recent years, however, since a tolerance error of the dilution ratio is required to be within 0.5% and in some cases within 0.1%, the error of 1% mentioned above exceeds the admissible range.

Citation List

Patent Literature

Patent Literature 1: JP-A-Heisei 03-218436

SUMMARY OF INVENTION

Technical Problem

The present invention has been made to solve the problem mentioned above, and an essential object thereof is to provide a gas analyzer and a gas analyzing system for introducing and analyzing a part of a measurement target gas flowing through a flow passage of the measurement target gas, wherein, even though the introduced measurement target gas is diluted and absorbed, a flow rate in the flow passage of the measurement target gas can be compensated so as to ensure accuracy in controlling the measurement target gas flowing through the measurement target gas flow passage and accuracy in its own and other measurements.

Solution to Problem

That is, a gas analyzer according to one aspect of the present invention includes: a gas introduction port communicating with a shunt point provided in a measurement target gas flow passage so that a part of the measurement target gas flowing through the measurement target gas flow passage is introduced; an object measurement device adapted to acquire the measurement target gas introduced from the gas introduction port so as to measure a quantity or concentration of a measurement object contained in the measurement target gas; an acquired gas flow rate measurement device adapted to measure a flow rate of the measurement target gas acquired by the object measurement device; and a gas supply device adapted to supply another gas of a flow rate equal to the gas flow rate measured by the acquired gas flow rate measurement device to a downstream side of the shunt point in the measurement target gas flow passage.

A gas analyzing system according to another aspect of the present invention includes: a measurement target gas flow passage in which a measurement target gas flows; a constant flow rate instrument provided on the measurement target gas flow passage in order to keep a constant flow rate of the measurement target gas flowing through the measurement target gas flow passage so that the constant flow rate of the measurement target gas is passed; a branched flow passage branched from a shunt point provided in an upstream side of the constant flow rate instrument in the measurement target gas flow passage; a gas introduction port connected to the branched flow passage so that a part of the measurement target gas is introduced; an object measurement device adapted to acquire the measurement target gas introduced from the gas introduction port so as to measure a quantity or concentration of a measurement object contained in the measurement target gas; an acquired gas flow rate measurement device adapted to measure a flow rate of the measurement target gas acquired by the object measurement device; and a gas supply device adapted to supply another gas of a flow rate equal to the gas flow rate measured by the acquired gas flow rate measurement device to a portion between a downstream side of the shunt point and an upstream side of the constant flow rate instrument in the measurement target gas flow passage.

According to the present invention described above, even though the object measurement device is adapted to dilute and absorb the acquired measurement target gas, since another gas having a flow rate equal to the acquired flow rate is supplied to the measurement target gas flow passage, the flow rate introduced into the measurement target gas flow passage and the flow rate derived therefrom are matched so that it becomes possible to ensure accuracy in controlling the flow rate of the gas introduced into the measurement target gas flow passage and derived therefrom as well as measurement accuracy of the measurement object.

In the object measurement device, it is preferable that, in the case where a part of the measurement target gas introduced from the gas introduction port is acquired, another gas is added to the rest of the measurement target gas introduced from the gas introduction port so as to supply the resultant gas to the downstream side of the shunt point in the measurement target gas flow passage. This is because the components of the supplied gas are close to those of the original gas as possible so that an effect on the measurement accuracy in such a case of setting, e.g., another measurement device can be minimized and the gas flow rate can be more accurately controlled.

As a specific aspect for attaining a remarkable effect of the present invention, it may be exemplified to have a configuration that includes: an exhaust gas flow passage into which a part of an exhaust gas exhausted from an internal combustion engine is introduced; a dilution gas flow passage into which a dilution gas is introduced in order to dilute the exhaust gas; a measurement target gas flow passage in which the exhaust gas flowing into the exhaust gas flow passage and the dilution gas flowing into the dilution gas flow passage are joined together and a resultant mixed gas thereof serving as a measurement target gas flows therein; a constant flow rate instrument provided on the measurement target gas flow passage in order to keep a constant flow rate of the measurement target gas flowing through the measurement target gas flow passage so that the constant flow rate of the measurement target gas is passed; a branched flow passage branched from a shunt point provided in an upstream side of the constant flow rate instrument in the measurement target gas flow passage; a gas introduction port connected to the branched flow passage so that a part of the measurement target gas is introduced; an object measurement device adapted to acquire the measurement target gas introduced from the gas introduction port so as to measure a quantity or concentration of a measurement object contained in the measurement target gas; an acquired gas flow rate measurement device adapted to measure a flow rate of the measurement target gas acquired by the object measurement device; and a gas supply device adapted to supply another gas of a flow rate equal to the gas flow rate measured by the acquired gas flow rate measurement device to a portion between a downstream side of the shunt point and an upstream side of the constant flow rate instrument in the measurement target gas flow passage.

According to the present invention, measurement accuracy of other measurement devices can be also improved. For example, the present invention may have a configuration that further includes: a flow rate control device adapted to control an inflow rate of the exhaust gas by controlling an inflow rate of the dilution gas so as to keep a flow rate ratio to be constant between the flow rate of the exhaust gas exhausted from the internal combustion engine and the exhaust gas flowing into the exhaust gas flow passage; and a collecting filter for passing through the measurement target gas flowing in a downstream side of the branched point of the measurement target gas flow passage and collecting particulate matter contained in the measurement target gas, so that a mass of the particulate matter contained in the exhaust gas exhausted from the internal combustion engine can be calculated based on the mass of the particulate matter collected by the collecting filter and the flow rate ratio. With this configuration, the inflow rate of the exhaust gas can be accurately controlled and accordingly, it becomes also possible to improve the measurement accuracy of measuring a mass of the particulate matter contained in the exhaust gas by a filter collecting method.

As a specific example of the object measurement device, it may be exemplified to have a configuration that includes a dilution mechanism for diluting the acquired measurement target gas and a particle number counting mechanism for counting the number of particles of the particulate matter contained in the measurement target gas diluted by the dilution mechanism.

Advantageous Effects of Invention

According to the present invention with the configuration as described above, even though the object measurement device is adapted to dilute and absorb the acquired measurement target gas, since another gas having a flow rate equal to the acquired flow rate is supplied to the measurement target gas flow passage, the flow rate introduced into the measurement target gas flow passage and the flow rate derived therefrom are matched so that it becomes possible to ensure accuracy in controlling the flow rate of the gas introduced into the measurement target gas flow passage and derived therefrom as well as measurement accuracy of the measurement object.

DESCRIPTION OF EMBODIMENTS

The following describes one embodiment of a gas analyzing system 100 according to the present invention referring to the accompanying drawings.

Figure 1:
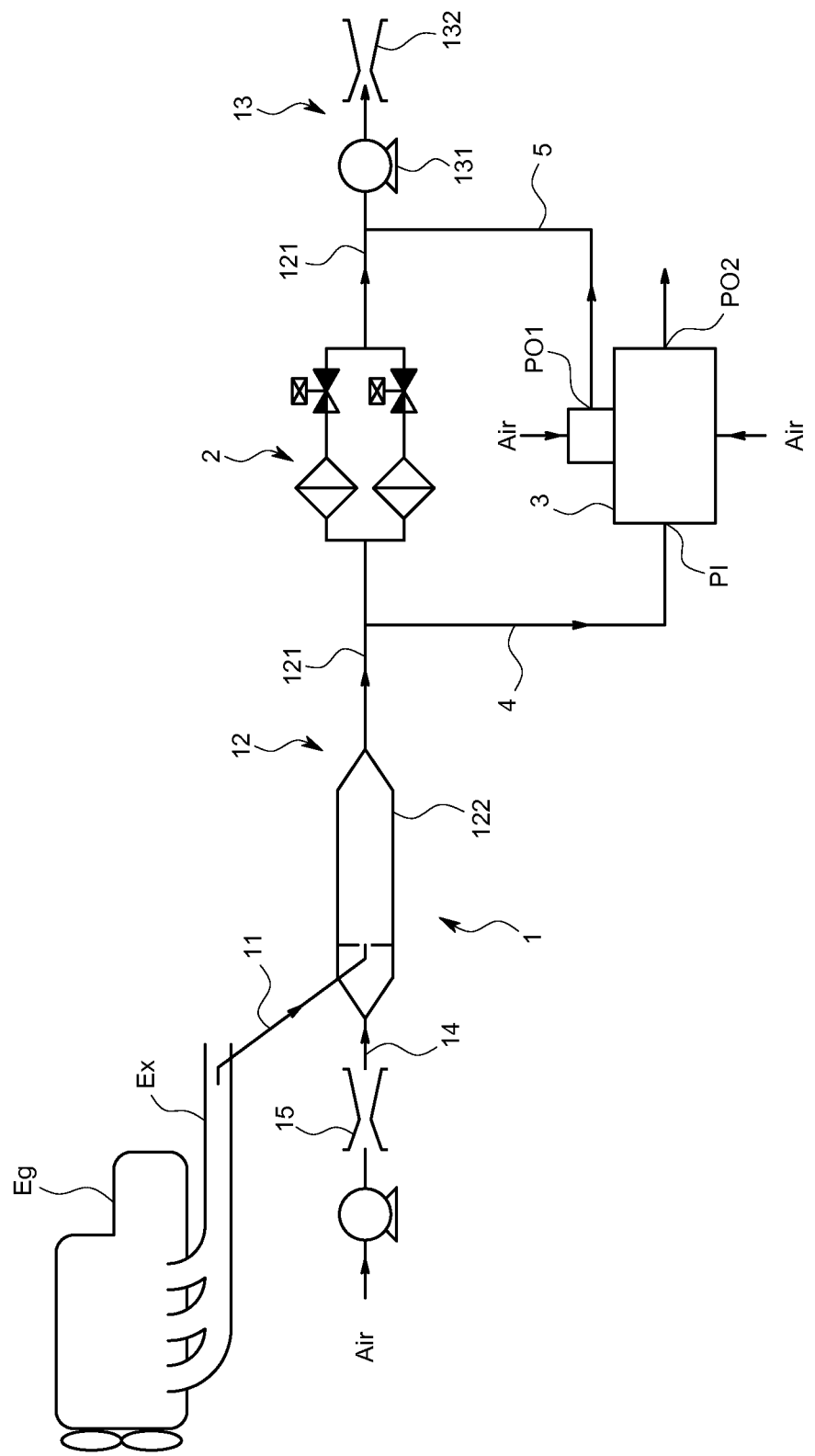
FIG. 1 is an overall configuration diagram of a gas analyzing system according to one embodiment of the present invention.

The gas analyzing system 100 according to the present embodiment is adapted to measure particulate matter (PM) contained in an exhaust gas discharged from an internal combustion engine Eg. As shown in FIG. 1, the device 100 basically includes a flow rate control mechanism 1 which is adapted to produce a mixed gas, i.e., a measurement target gas by mixing a dilution gas (i.e., air in this example) with the exhaust gas so as to render the mixed gas to flow at a constant flow rate and to control an inflow rate of the dilution gas to thereby control an inflow rate of the exhaust gas, and further includes a collecting filter 2 which is provided on the measurement target gas flow passage (also, referred to as "mixed gas flow passage 12" hereinafter) through which the mixed gas flows so as to collect particulate matter (PM) contained in the mixed gas. Each part thereof is described below in detail.

The flow rate control mechanism 1 includes an exhaust gas flow passage 11 which is inserted to an exhaust pipe Ex of the internal combustion engine Eg so that a part of the exhaust gas flows therein, a dilution gas flow passage 14 through which the dilution gas flows, the mixed gas flow passage 12 which is commonly connected to the exhaust gas flow passage 11 and the dilution gas flow passage 14 so that the exhaust gas and the dilution gas are mixed, and a constant flow rate instrument 13 which is provided at an end portion of the mixed gas flow passage 12.

The mixed gas flow passage 12 includes a mixer 122 such as so-called a mini-tunnel or micro-tunnel in addition to a normal pipe 121. The constant flow rate instrument 13 includes a suction pump 131 such as e.g. a roots-blower and a critical orifice 132 connected to a downstream of the suction pump 131 so that the gas is passed therethrough at a constant flow rate. Herein, the flow rate determined by the constant flow rate instrument 13 is, e.g., 50 L/min.

A flow rate controller 15 such as a variable orifice is attached to a start edge portion of the dilution gas flow passage 14 so as to adjust an inflow rate of the dilution gas to the mixed gas flow passage 12, and a flow rate meter (not shown) is also attached to the exhaust pipe Ex for measuring a flow rate of the exhaust gas flowing through the exhaust pipe Ex.

In this configuration, the flow rate control mechanism 1 is controlled by a command from an electronic control circuit such as a computer (not shown) in order that, for example, a flow rate ratio between the flow rate of the exhaust gas flowing through the exhaust pipe Ex and the flow rate of the exhaust gas flowing through the measurement target gas flow passage is made constant so as to control the inflow rate of the dilution gas to the mixed gas flow passage 12.

The collecting filter 2 is provided downstream of the mixer 122 in the mixed gas flow passage 12 so that the mixed gas flowing through the mixed gas flow passage 12 at this installation portion are entirely passed through so as to collect the particulate matter PM contained in the mixed gas. The collecting filter 2 is known one and a detailed explanation of a material etc. thereof is omitted here.

Thus, a mass of the particulate matter PM contained in the exhaust gas discharged from the internal combustion engine Eg can be calculated based on the mass of the particulate matter PM collected by the collecting filter 2. That is, as described above, since a ratio of the flow rate $q_{TOTAL}$ of the exhaust gas flowing through the exhaust pipe Ex (i.e., the total flow rate of the exhaust gas discharged from the internal combustion engine Eg) to a flow rate $q_{PART}$ of the exhaust gas flowing through the measurement target gas flow passage is kept constant, assuming that the ratio $R = q_{TOTAL}/q_{PART}$, and the mass of the particulate matter PM collected by the collecting filter 2 is $m_{TRAP}$, the mass $m_{TOTAL}$ of the particulate matter PM contained in the exhaust gas discharged from the internal combustion engine Eg can be represented as $m_{TOTAL} = R \cdot m_{TRAP}$. Hence, the mass of the particulate matter PM contained in the exhaust gas can be calculated based on the mass of the particulate matter PM collected by the collecting filter 2.

In addition to the above configuration, in the present embodiment, a gas analyzer 3 is further provided in order that a part of the mixed gas flowing through the mixed gas flow passage 12 is shunted so as to measure the particulate matter PM which is an object to be measured (referred to as "measurement object" hereinafter) contained in the mixed gas.

Figure 2:
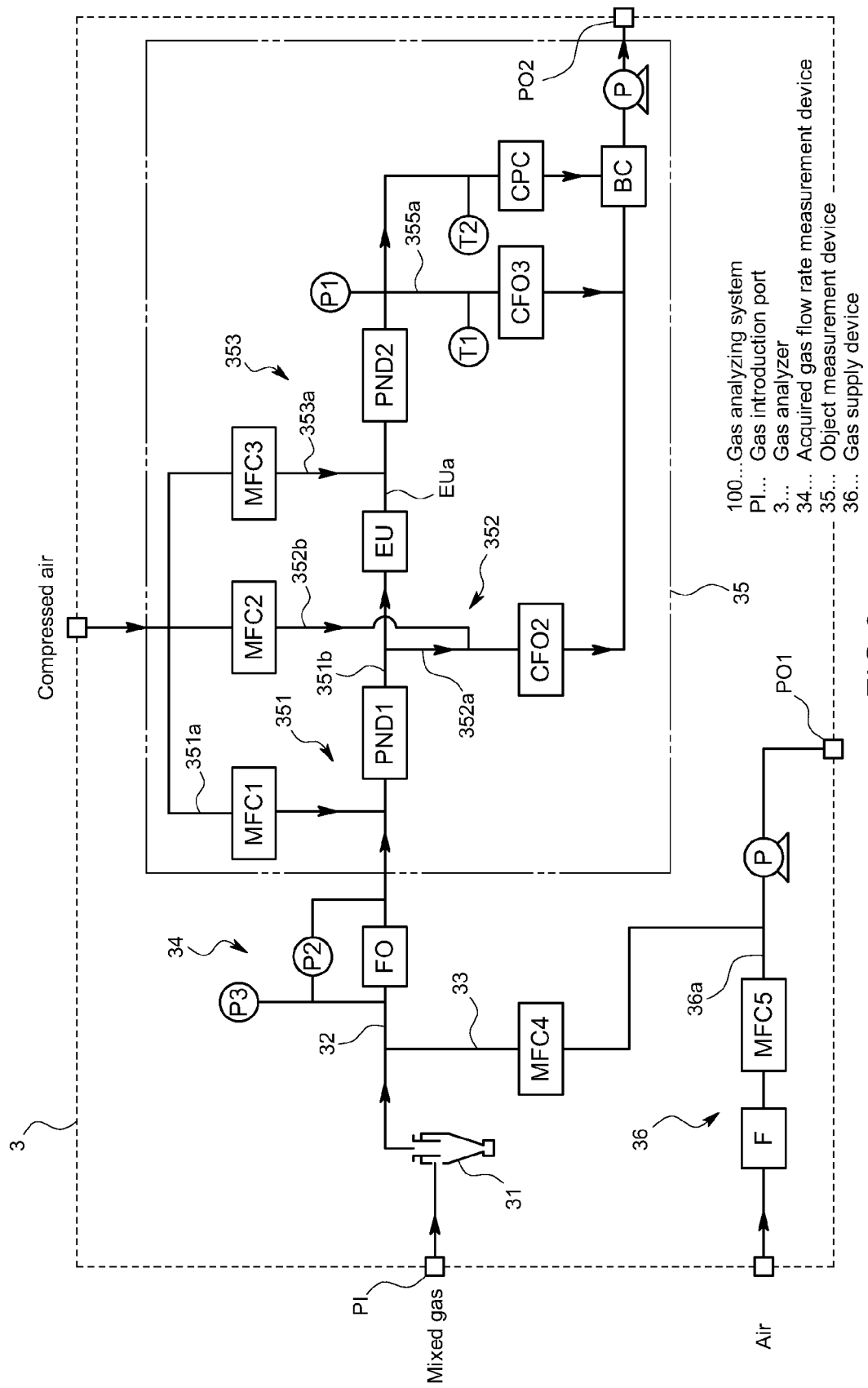
FIG. 2 is an internal fluid circuit diagram of a gas analyzer in the same embodiment.

As shown in FIGS. 1 and 2, the gas analyzer 3 includes a gas introduction port PI which is connected to an end of a branch flow passage 4 branched from an upstream side of the collecting filter 2 in the mixed gas flow passage 12, an object measurement device 35 which takes in a part of the mixed gas introduced from the gas introduction port PI so as to count a particle number of the particulate matter PM contained in the mixed gas, an acquired gas flow rate measurement device 34 adapted to measure a flow rate of the mixed gas acquired by the object measurement device 35, and a gas supply device 36 adapted to supply another gas of a flow rate equal to the gas flow rate measured by the acquired gas flow rate measurement device 34 back to the mixed gas flow passage 12.

An internal structure of the gas analyzer 3 is described in detail referring to FIG. 2. After dusts contained in the mixed gas led to the gas introduction port PI are removed by a dust removal device (such as, e.g., a cyclone) 31, the mixed gas is shunted into a bypass flow passage 33 and a sampling flow passage 32.

Most (about 95% to 99%) of the mixed gas flowing into the gas introduction port PI is led to the bypass flow passage 33 and is derived as it is to the outside from a first gas derivation port PO1. The flow rate of the mixed gas flowing through the bypass flow passage 33 is controlled to be constant (e.g., 10 L/min in this example) by a constant flow rate instrument such as a mass flow controller MFC4. Further, the first gas derivation port PO1 is communicated with a portion between the constant flow rate instrument 13 and the collecting filter 2 in the mixed gas flow passage 12 through a connecting passage 5. Thus, most of the mixed gas shunted from the mixed gas flow passage 12 to the branch flow passage 4 and flowing into the gas analyzer 3, that is, the mixed gas except the mixed gas introduced into the sampling flow passage 32 is supplied again to the mixed gas flow passage 12 through the bypass flow passage 33 and through the connecting passage 5 and then flows into the constant flow rate instrument 13 of the mixed gas flow passage 12. It is noted here that a symbol P provided on the bypass flow passage 33 denotes a pump for forcibly leading the mixed gas to flow toward the mixed gas flow passage 12.

The remaining mixed gas (in this case, 0.1 to 0.5 L/min, i.e., about 1% to 5%) flowing into the sampling flow passage 32 is led to the object measurement device 35 via the acquired gas flow rate measurement device 34.

The acquired gas flow rate measurement device 34 includes, e.g., a fluid resistance (orifice, in this case) FO provided on the sampling flow passage 32 and pressure gages P2 and P3 for measuring a pressure difference before and after the fluid resistance FO and an absolute pressure in the downstream side thereof. Thus, the flow rate of the gas flowing through the sampling flow passage 32 can be calculated based on the measurement pressures measured by the pressure gages P2 and P3.

The object measurement device 35 is provided with a first dilution mechanism 351, a shunt rate control mechanism 352, an evaporator unit EU and a second dilution mechanism 353 in this order from the upstream and a particle number counting mechanism CPC is arranged thereafter for counting the particle number of the particulate matter PM.

The first dilution mechanism 351 includes a first dilution passage 351a which is connected to the sampling flow passage 32 to which the dilution gas (i.e., air, in this case) is introduced and a first mixer PND1 which is provided downstream of the connecting point thereof. A mass flow controller MFC1 is provided on the first dilution passage 351a so that the inflow rate of the dilution gas can be controlled.

The shunt rate control mechanism 352 is adapted to shunt a part of the dilution mixed gas outputted from the first dilution mechanism 351 so as to exhaust the same to the outside from the second gas derivation port PO2 and lead the rest thereof to an evaporator unit EU. Specifically, the shunt rate control mechanism 352 includes a first shunt passage 352a which is branched from an output flow passage 351b of the first dilution mechanism 351, a constant flow rate instrument (i.e., a critical orifice, in this case) provided on the first shunt passage 352a, a flow rate control gas introduction passage 352b connected to an upstream side of the constant flow rate instrument CFO2 on the first shunt passage 352a, and a mass flow controller MFC2 provided on the flow rate control gas introduction passage 352b. Thus, the flow rate of the flow rate control gas (i.e., air, in this case) fed into the first shunt passage 352a from the flow rate control gas introduction passage 352b is controlled by the mass flow controller MFC2 so as to be able to indirectly control the flow rate of the mixed gas flowing into the first shunt passage 352a from output flow passage 351b of the first dilution mechanism 351.

The evaporator unit EU is a carburetor which is provided for the purpose of removing volatile particles in this case.

The second dilution mechanism 353 is adapted to further dilute the dilution mixed gas outputted from the evaporator unit EU and it includes a second dilution passage 353a which is connected to an output passage EUa of the evaporator unit EU so as to lead a dilution gas (i.e., air, in this case) to flow therein and a second mixer PND2 provided downstream of the connecting point thereof. A mass flow controller MFC3 is provided on the second dilution passage 353 so as to control the inflow rate of the dilution gas.

A part of the mixed gas diluted through the first dilution mechanism 351 and the second dilution mechanism 353 etc. is led to a second shunt passage 355a at a constant flow rate and is exhausted from a second gas exhaust port PO2 through a constant flow rate instrument CFO3 (i.e., a critical orifice, in this case), and the rest thereof is led to the particle number counting mechanism CPC.

The particle number counting mechanism CPC is adapted to mix a supersaturated organic gas such as, e.g., alcohol or butanol to be adhered to the particulate matter contained in the exhaust gas so that the particulate matter is grown to have a large diameter and the grown particulate matter PM is exhausted from a slit and the number of the exhausted particles is counted by applying laser beams. It is noted here that symbols T1 and T2 are thermometer, P1 is a pressure gauge and BC is a buffer tank.

In this configuration, a dilution ratio indicating a degree of dilution that the mixed gas introduced into the particle number counting mechanism CPC is diluted from the pre-diluted mixed gas firstly flowing into the sampling flow passage 32 can be calculated based on the introduction flow rate of the pre-diluted mixed gas measured by the acquired gas flow rate measurement device 34 and a flow rates of the respective mass flow controllers MFC1 to MFC3, and the flow rate of the mixed gas introduced to the particle number counting mechanism CPC can be calculated based on the temperature and pressure measured by the thermometer T2 and the pressure gauge P1 which are provided upstream thereof. Therefore, the particle number of the particulate matter PM contained in the pre-diluted mixed gas first flowing into the sampling flow passage 32 can be calculated based on these factors.

In the present embodiment, the flow rate of the pre-diluted mixed gas first flowing into the sampling flow passage 32 can be also calculated by flow rate controls executed by the respective mass flow controllers MFC1 to MFC3.

In this configuration, the gas supply device 36 which is a specific feature in configuration of the present embodiment is adapted to supply another gas (i.e., air, in this case) of a flow rate equal to the flow rate of the mixed gas acquired by the object measurement device 35 to the downstream side of a shunt point in the mixed gas flow passage 12.

In specific, as shown in FIG. 2, the gas supply device 36 includes another gas supply passage 36a for supplying another gas to the bypass flow passage 33 and a flow rate control unit MFC5 (i.e., a mass flow controller, in this case) which is provided on another gas supply passage 36a for controlling a supply flow rate of another gas. Note that a symbol F in FIG. 2 denotes a filter.

Another gas supply passage 36a is connected to a portion between a downstream of the constant flow rate instrument and an upstream of the pump on the bypass flow passage 33 so that another gas supplied through another gas supply passage 36a is joined with the mixed gas which is not supplied to the object measurement device 35 of the mixed gas introduced from the gas introduction port PI, i.e., the mixed gas flowing through the bypass flow passage 33, and the resultant mixed gas flows into the constant flow rate instrument 13 of the mixed gas flow passage 12 through the first gas derivation port PO1 and through the connecting passage 5.

The flow rate of the mixed gas measured by the acquired gas flow rate measurement device 34 is given to the flow rate control unit MFC5 as a target value so that the air of the target flow rate is fed into the connecting passage 5 through another gas supply passage 36a.

With this configuration, the gas of the flow rate equal to that of the mixed gas shunted in the middle of the mixed gas flow passage 12, i.e., at an upstream of the collecting filter 2 and fed to the gas analyzer 3 is supplied to the downstream of the collecting filter 2 in the mixed gas flow passage 12 to be led to flow into the constant flow rate instrument 13. Therefore, the total flow rate of the exhaust gas which flows into the mixed gas flow passage 12 to serve as the mixed gas and the dilution gas can be precisely matched with the gas flow rate derived from the mixed gas flow passage 12.

As a result, in this embodiment, it becomes possible to very accurately control the inflow rate of the exhaust gas by the flow rate control mechanism 1. Further, it becomes possible to accurately control a dilution ratio of the exhaust gas and the dilution gas to be introduced to the mixer 122 and to accurately keep a ration of the flow rate of the exhaust gas flowing through the exhaust pipe Ex and the flow rate of the exhaust gas shunted from the exhaust pipe Ex, or as a result of this, it becomes possible to very accurately measure the mass of the particulate matter PM collected by the collecting filter 2. It is noted that the present invention is not limited to the present embodiment as described above.

Figure 3:
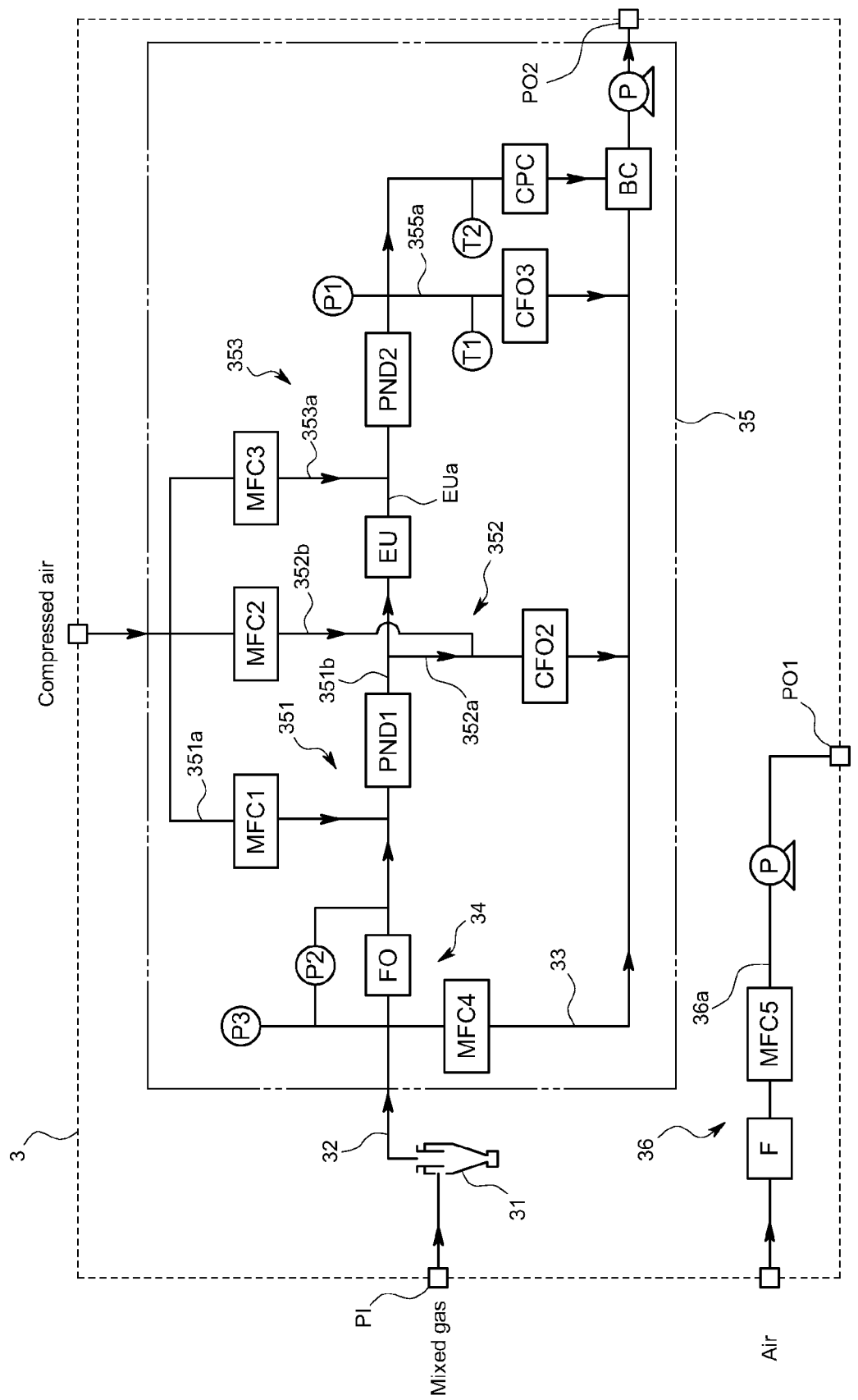
FIG. 3 is an internal fluid circuit diagram of a gas analyzer according to another embodiment of the present invention.

For example, as shown in FIG. 3, the mixed gas introduced into the gas analyzer 3 may be entirely used as another gas (e.g., air) so as to be supplied back to the mixed gas flow passage 12. In this case, the gas analyzer 3 and the object measurement device 35 can be regarded as synonymous with each other, and the acquired gas flow rate measurement device 34 includes the mass flow controller MFC4 as an constituent element thereof in addition to, e.g., the fluid resistance (i.e., orifice in this case) FO and the pressure gauges P2 and P3. Moreover, in FIG. 3, by using, e.g., compressed air to be introduced as a heat gas, the pump P between the mass flow controller MFC5 and the first gas introduction port PO1 can be omitted.

Moreover, the measurement target gas may be not only the mixed gas of the exhaust gas and the dilution gas but also the exhaust gas per se which is not diluted. This aspect is considered to be preferred in a vehicle-mounted type a gas analyzer and the like. Further, as the measurement target gas, it may be possible to apply not only the exhaust gas of the internal combustion engine but also various gases such as gases introduced to and derived from a combustion engine such as a boiler or a chemical reaction furnace.

In addition, the dilution gas is not only air but also such as, e.g., an inert gas may be used. In short, in the present invention, various gases including the mixed gas of the measurement target gas added with the other gas are regarded as another gas if not the measurement target gas per se, regardless of the kinds of the gases.

Moreover, the gas analyzer is not limited to those counting the particulate matter, and the present invention can be applied to various types of analyzers.

In addition, the present invention is not limited to the above embodiments, and it is needless to say that various changes and modifications can be made within the scope of the present invention unless departing from the spirit thereof.

INDUSTRIAL APPLICABILITY

According to the present invention, even though the object measurement device is adapted to dilute and absorb the acquired measurement target gas, since another gas having a flow rate equal to the acquired flow rate is supplied to the measurement target gas flow passage, the flow rate introduced into the measurement target gas flow passage and the flow rate derived therefrom are matched so as to ensure high accuracy of controlling the flow rate of the gas introduced into the measurement target gas flow passage and derived therefrom as well as measurement accuracy of the measurement object.

REFERENCE SIGNS LIST

100 . . . Gas analyzing system
PI . . . Gas introduction port
3 . . . Gas analyzer
34 . . . Acquired gas flow rate measurement device
35 . . . Object measurement device
36 . . . Gas supply device

The invention claimed is:

1. A gas analyzer comprising:
a gas introduction port communicating with a shunt point provided in a measurement target gas flow passage so that a part of the measurement target gas flowing through the measurement target gas flow passage is introduced;
an object measurement device adapted to acquire the measurement target gas introduced from the gas introduction port so as to measure a quantity or concentration of a measurement object contained in the measurement target gas;
an acquired gas flow rate measurement device adapted to measure a flow rate of the measurement target gas acquired by the object measurement device; and
a gas supply device adapted to supply another gas of a flow rate equal to the gas flow rate measured by the acquired gas flow rate measurement device to a downstream side of the shunt point in the measurement target gas flow passage.

2. The gas analyzer according to claim 1, wherein the object measurement device is adapted to acquire a part of the measurement target gas introduced from the gas introduction port, and
wherein the gas supply device is adapted to add another gas to the rest of the measurement target gas introduced from the gas introduction port so as to supply the resultant gas to the downstream side of the shunt point in the measurement target gas flow passage.

3. A gas analyzing system comprising:
a measurement target gas flow passage in which a measurement target gas flows;
a constant flow rate instrument provided on the measurement target gas flow passage in order to keep a constant flow rate of the measurement target gas flowing through the measurement target gas flow passage so that the constant flow rate of the measurement target gas is passed;
a branched flow passage branched from a shunt point provided in an upstream side of the constant flow rate instrument in the measurement target gas flow passage;
a gas introduction port connected to the branched flow passage so that a part of the measurement target gas is introduced;
an object measurement device adapted to acquire the measurement target gas introduced from the gas introduction port so as to measure a quantity or concentration of a measurement object contained in the measurement target gas;
an acquired gas flow rate measurement device adapted to measure a flow rate of the measurement target gas acquired by the object measurement device; and
a gas supply device adapted to supply another gas of a flow rate equal to the gas flow rate measured by the acquired gas flow rate measurement device to a portion between a downstream side of the shunt point and an upstream side of the constant flow rate instrument in the measurement target gas flow passage.

4. A gas analyzing system comprising:
an exhaust gas flow passage into which a part of an exhaust gas exhausted from an internal combustion engine is introduced;
a dilution gas flow passage into which a dilution gas is introduced in order to dilute the exhaust gas;
a measurement target gas flow passage in which the exhaust gas flowing into the exhaust gas flow passage and the dilution gas flowing into the dilution gas flow passage are joined together and a resultant mixed gas thereof serving as a measurement target gas flows therein;
a constant flow rate instrument provided on the measurement target gas flow passage in order to keep a constant flow rate of the measurement target gas flowing through the measurement target gas flow passage so that the constant flow rate of the measurement target gas is passed;

a branched flow passage branched from a shunt point provided in an upstream side of the constant flow rate instrument in the measurement target gas flow passage;

a gas introduction port connected to the branched flow passage so that a part of the measurement target gas is introduced;

an object measurement device adapted to acquire the measurement target gas introduced from the gas introduction port so as to measure a quantity or concentration of a measurement object contained in the measurement target gas;

an acquired gas flow rate measurement device adapted to measure a flow rate of the measurement target gas acquired by the object measurement device; and a gas supply device adapted to supply another gas of a flow rate equal to the gas flow rate measured by the acquired gas flow rate measurement device to a portion between a downstream side of the shunt point and an upstream side of the constant flow rate instrument in the measurement target gas flow passage.

5. The gas analyzing system according to claim 4 further comprising:

a flow rate control device adapted to control an inflow rate of the exhaust gas by controlling an inflow rate of the dilution gas so as to keep a flow rate ratio to be constant between the flow rate of the exhaust gas exhausted from the internal combustion engine and the exhaust gas flowing into the exhaust gas flow passage; and a collecting filter for passing through the measurement target gas flowing in a downstream side of the branched point of the measurement target gas flow passage and collecting particulate matter contained in the measurement target gas, wherein a mass of the particulate matter contained in the exhaust gas exhausted from the internal combustion engine can be calculated based on the mass of the particulate matter collected by the collecting filter and the flow rate ratio.

6. The gas analyzing system according to claim 4, wherein the object measurement device comprises a dilution mechanism for diluting the acquired measurement target gas and a particle number counting mechanism for counting the number of particles of the particulate matter contained in the measurement target gas diluted by the dilution mechanism.

* * * * *